United States Patent [19]

Lopes

[11] Patent Number: 5,143,720
[45] Date of Patent: Sep. 1, 1992

[54] DISINFECTING AND SANITIZING COMPOSITIONS

[75] Inventor: John A. Lopes, Troy, Mich.

[73] Assignee: Microcide, Inc., Troy, Mich.

[21] Appl. No.: 619,245

[22] Filed: Nov. 28, 1990

[51] Int. Cl.$^5$ .......................... A61K 7/24; A61K 7/16
[52] U.S. Cl. ........................................ 424/55; 424/49; 424/44; 424/56
[58] Field of Search .................. 424/55, 56, 49, 44

[56] References Cited

U.S. PATENT DOCUMENTS

| | | | |
|---|---|---|---|
| 3,431,339 | 3/1969 | Gyarmathy et al. | 424/49 |
| 3,518,343 | 6/1970 | Welsh et al. | 424/44 |
| 3,629,468 | 12/1971 | Anderson | 424/44 |
| 3,772,431 | 11/1973 | Mlkvy et al. | 424/44 |
| 3,888,976 | 6/1975 | Mlkvy et al. | 424/49 |
| 3,919,408 | 11/1975 | Mitchell et al. | 424/44 |
| 3,947,566 | 3/1976 | Sarna | 424/45 |
| 3,962,417 | 6/1976 | Howell | 424/56 |
| 4,088,597 | 5/1978 | Morlock et al. | 424/670 |
| 4,108,981 | 8/1978 | Muhler et al. | 424/55 |
| 4,150,151 | 4/1979 | Pader et al. | 424/56 |
| 4,213,961 | 7/1980 | Curtis et al. | 424/55 |
| 4,256,731 | 3/1981 | Curtis et al. | 424/55 |
| 4,477,438 | 10/1984 | Wilcockson et al. | 424/616 |
| 4,545,979 | 10/1985 | Ambike et al. | 424/56 |
| 4,550,018 | 10/1985 | Ambike et al. | 424/56 |
| 4,627,972 | 12/1986 | Gioffre et al. | 424/49 |
| 4,925,655 | 5/1990 | Smigel et al. | 424/52 |
| 4,945,110 | 7/1990 | Brokken et al. | 514/517 |
| 4,961,923 | 10/1990 | Heyde | 424/55 |
| 4,980,152 | 12/1990 | Frazier et al. | 424/52 |
| 5,008,106 | 4/1991 | Merianus et al. | 424/80 |

OTHER PUBLICATIONS

C.A. 113:39166k (Tagagi) (1989) of JP 01305007 Dec. 8, 1989.
C.A. 107:6464h (1987) (Advanced Care Healthscope) of JP 62070311 Mar. 31, 1987.
C.A. 107:46042n (1987) (Sarsunova) of Czech. 226096 Jun. 1, 1986.
C.A. 104:230273m (1986) Aberg) Gt. Br. 2163348 Feb. 26, 1986.
C.A. 86:96010c (1976) (Morlock) Ger. 2527795 Dec. 23, 1976.

*Primary Examiner*—Shep K. Rose
*Attorney, Agent, or Firm*—Krass & Young

[57] ABSTRACT

Anhydrous sanitizing and disinfecting concentrate compositions having excellent shelf life and chemical stability comprise less than 0.1 weight percent water; an anionic surfactant present in an amount of from about 0.05 weight percent to about 10.0 weight percent, and an acidic component, present in an amount effective to produce a pH of below pH 5.0 upon dilution with water.

Between about 0.25 parts by weight to about 7.5 parts by weight of the concentrate compositions are diluted with sufficient water to make 100 parts by weight of an aqueous solution having excellent antimicrobial activity against gram positive and gram negative bacteria.

10 Claims, No Drawings

DISINFECTING AND SANITIZING COMPOSITIONS

TECHNICAL FIELD

This invention relates to sanitizing and disinfecting compositions. More particularly, the present invention concerns anhydrous sanitizing and disinfecting concentrate compositions suitable for dilution in water to produce aqueous antimicrobial solutions, particularly suited for use as mouthwashes, in human and animal hygiene, and as fresh fruit and vegetable sanitizers, and sanitizers for food processing and other equipment.

BACKGROUND OF THE INVENTION

Many sanitizing and disinfecting compositions are known in the art which employ a variety of substances as the active antimicrobial agent. For example, U.S. Pat. No. 4,647,458 to Uemo, et al. discloses mixtures of ethyl alcohol and organic acids as bactericides for food and food processing machinery and utensils. U.S. Pat. No. 3,867,300 to Karabinos, et al. discloses aqueous bactericidal compositions containing an aliphatic monocarboxylic acid of from eight to eleven carbon atoms and a non-ionic or anionic surfactant. British Patent specification 917,432 to Pennwalt Chemicals Corp. discloses sanitizing compositions comprising an alkyl aryl sulfonic acid or salt thereof, together with an acid component to generate a pH of between about pH 1.5 and pH 3.5 upon dilution in water. U.S. Pat. No. 4,404,040 to Wang discloses sanitizing concentrate compositions comprising an aliphatic short chain fatty acid, a hydrotrope or solubilizer for the fatty acid, and an acid to produce a pH between pH 2 and pH 5 when diluted with water. U.S. Pat. No. 4,715,980 to Lopes, et al. discloses concentrated antimicrobial sanitizing compositions for dilution in water comprising a dicarboxylic acid and an acidic component capable of generating a pH below about pH 5 upon dilution.

Aqueous sanitizing and disinfecting compositions which contain an anionic surfactant and an acidic component generally have short shelf lives because most surfactants lack the requisite stability in acidic aqueous solution. It is therefore an object of the present invention to provide sanitizing and disinfecting compositions in stable concentrated form which are suitable for dilution in water or other suitable solvent for use as oral disinfectants and as sanitizing and disinfecting agents which are safe for use as mouthwashes, for human and animal hygiene, and for sanitizing food or food handling and processing equipment.

SUMMARY OF THE INVENTION

The present invention provides sanitizing and disinfecting compositions which have the following advantages: a) shelf-stability while containing acid-unstable anionic surfactants; b) low cost of formulation (only concentrated chemical components are used); c) cost savings in transporting and storing the finished formulations (the bulk of water is excluded); d) elimination of the difficulties in preparing concentrated aqueous formulations with ingredients of low aqueous solubility; e) novel non-aqueous formulations for personal hygiene; f) convenience in carrying personal sanitizers; and g) utility for direct use on raw foods. Moreover, the concentrate formulations of the present invention do not have the instability problems associated with concentrated aqueous formulations at low temperatures.

In accordance with the present invention there are provided sanitizing and disinfecting concentrate compositions having excellent shelf life and chemical stability. The concentrates are capable of dilution with water to form an antimicrobial solution, with the concentrate composition comprising, prior to dilution, a) an anionic surfactant present in an amount of from about 0.25 weight percent to about 10.0 weight percent, b) an acidic component, present in an amount effective to produce a pH of below pH 5.0 upon dilution with water; the concentrate composition comprising less than 0.1 weight percent water.

In one embodiment, the concentrate compositions of the present invention are in the form of a solid dry compositions suitable for dilution with water just prior to use. In another embodiment, the concentrate compositions of this invention are in the form of a liquid mixture in an anhydrous liquid carrier. The acidic component of these compositions may function both to lower the pH upon dilution with water and as the anhydrous liquid carrier for the other components.

DETAILED DESCRIPTION

The anhydrous sanitizing and/or disinfecting compositions of this invention comprise an anionic surfactant agent and an acidic component, both of which are miscible with water at low concentrations. The compositions contain less than 0.1% by weight water, and are capable of forming, upon dilution with water, an acidic aqueous antimicrobial solution having a pH below about pH 5.0. The compositions exhibit excellent shelf life and have exceptional activity against gram positive and gram negative bacteria such as *E. coli* and *Staph. aureus*.

The compositions may be in a dry, powdered form or, alternatively, in a liquid form in an anhydrous carrier in which the active components of the mixture are miscible. In certain embodiments of the present invention, the acidic component of the compositions serves a dual role as both acidic component and anhydrous carrier. However, regardless of their physical form, the sanitizing and disinfecting compositions of this invention are formulated of ingredients which are readily miscible with water at low concentrations and are thus suitable for easy use by mixing with water just prior to use.

Depending upon the end use for which the compositions of this invention are intended, the compositions may further contain components such as gums, flavoring agents, sweeteners, coloring agents, and inorganic or organic salts. For example, when used as oral rinses or mouthwashes, the sanitizing and disinfecting compositions of the present invention optionally contain sweeteners, colorants, and flavoring agents in addition to the surfactant and acidic components. When used for disinfecting hands, skin or hair, the formulations of the present invention optionally contain emolients or conditioning agents. In formulations containing a nonaqueous carrier, the carrier may provide the emolient and condition functions.

The anionic surfactant agent, acidic components, flavoring agents, gums, colorants, sweeteners, and salts utilizable in the compositions of this invention are selected from the class of substances generally regarded as safe (GRAS) or which have been ascribed food additive status as those terms are defined by the United States Food and Drug Administration in the Code of Federal Regulations, Chapter 21, Parts 178, 182 and 184, or which have low toxicity and have been approved for specific uses by the regulatory agencies.

Suitable anionic surfactant materials for use in this the compositions of this invention include the the ammonium, sodium, potassium, calcium and magnesium salts of (a) $C_6$–$C_{18}$ alkyl- and alkenylsulfates; (b) $C_6$–$C_{18}$ alkyl- and alkenyl ether sulfates; (c) $C_8$–$C_{16}$ alkyl diphenyl ether disulfonates; (d) $C_4$–$C_{18}$ fatty acid isethionates; (e) $C_6$–$C_{18}$ alkyl- and alkenylsulfonates; (f) dialkyl- and dialkenyl sulfosuccinates in which the alkyl or alkenyl groups independently contain from six to eighteen carbon atoms; (g) alkylbenzenesulfonates in which the alkyl group contain from six to eighteen carbon atoms; (h) naphthalenesulfonates; (i) alkylnaphthalenesulfonates in which the alkyl group contains from one to six carbon atoms; (j) the mono-(n-alkyl) and mono-(n-alkenyl) acyl esters of $C_2$–$C_4$ hydroxylated monocarboxylic acids, in which the alkyl or alkenyl group contains from six to eighteen carbon atoms; (k) the mono-(n-alkyl) and mono-(n-alkenyl) acyl esters of $C_2$–$C_4$ hydroxylated dicarboxylic acids, in which the alkyl or alkenyl group contains from six to eighteen carbon atoms; (l) the mono-(n-alkyl) and mono-(n-alkenyl) alkyl esters of $C_2$–$C_4$ dicarboxylic acids, in which the alkyl or alkenyl group contains from six to eighteen carbon atoms, and (m) $C_4$–$C_{18}$ fatty alcohol sulfoacetates.

By the term "alkyl" as used throughout this specification and the appended claims is meant a monovalent straight or branched chain hydrocarbon radical which can be thought of as derived from a saturated acyclic hydrocarbon by the removal of one hydrogen atom. By the term "alkenyl" is meant a monovalent hydrocarbon radical containing one or more carbon-carbon double bonds, which radical, can be thought of as being derived from an unsaturated acyclic hydrocarbon by the removal of one hydrogen atom.

The term, "salt of a mono-(n-alkyl) or mono-(n-alkenyl) acyl ester of $C_2$–$C_4$ hydroxylated monocarboxylic acids" means an ester-salt of a hydroxylated monocarboxylic acid, such as lactic acid, which has been formed by esterification of its hydroxyl function by another acid, and in which its carboxyl function has been converted to a carboxylate salt. An example of such a compound is so-called "octyl lactylate" which is the ester formed by esterifying the hydroxyl group of lactic acid with octanoic acid, and converting the carboxyl function of the lactic acid portion of the resulting ester to the carboxylate salt form.

Similarly, the term, "salt of a mono-(n-alkyl) or mono-(n-alkenyl) acyl ester of $C_2$–$C_4$ hydroxylated dicarboxylic acids" means an ester-salt of a hydroxylated dicarboxylic acid, such as hydroxymalonic acid, which has been formed by esterification of its hydroxyl function by another acid, and in which its two carboxyl functions have been converted to carboxylate salts.

By the term "salt of a mono-(n-alkyl) or mono-(n-alkenyl) alkyl ester of $C_2$–$C_4$ dicarboxylic acids" is meant an ester-salt of a dicarboxylic acid, such as succinic acid, which has been formed by esterification by an alcohol at one carboxyl function, and in which its other carboxyl function has been converted to a carboxylate salt.

Preferred anionic surfactants for the compositions of the present invention include the ammonium, sodium, and potassium salts of 1,4-dihexyl sulfosuccinic acid; the ammonium, sodium, and potassium salts of dioctylsulfosuccinic acid; the ammonium, sodium, and potassium salts of laurylsulfuric acid, and octyl lactylate.

Suitable materials for use as the acidic component in the disinfecting and sanitizing compositions of this invention include acetic acid, adipic acid, ascorbic acid, citric acid, dehydroacetic acid, erythorbic acid, fumaric acid, glutaric acid, gluconic acid, hyaluronic acid, hydroxyacetic acid, lactic acid, malic acid, succinic acid, sulfamic acid, tannic acid, tartaric acid, and mixtures thereof.

Suitable anhydrous solvents or carriers for the compositions of this invention are selected from propylene glycol, acetic acid, hydroxyacetic acid, and propionic acid.

Suitable sweetening agents for use in the compositions of the present invention include aspartame, dextrose, invert sugar, saccharin, sorbitol, and sucrose. Flavoring agents include those well known to practitioners of the pharmaceutical and formulation arts including artificial strawberry, cherry, raspberry, lemon and lime flavorants as well as menthol.

Components may also be included in the solid dry formulations of the present invention to act as sequestering agents or to reduce the cloudiness which might otherwise result when the compositions are dissolved in hard water. Components which may be employed in the compositions of this invention for this purpose include inorganic and organic salts such as sodium acid pyrophosphate and the chlorides, sulfates, citrates, nitrates, acetates, and lactates of potassium, sodium, ammonium, and zinc. For example, sodium sulfate is used in amounts ranging between about 50 and 85 weight percent and zinc sulfate or sodium citrate are used in amounts of about 30 weight percent in the dry solid compositions of this invention. While not adhering to any theory to the exclusion of others, it is believed that the sodium sulfate, zinc sulfate, and sodium citrate control cloudiness by controlling the critical micelle concentration of the resulting aqueous solutions. Similarly, sodium acid pyrophosphate is used in the dry solid compositions of this invention in concentrations ranging between about 30 and 50 weight percent. The sodium acid pyrophosphate is believed to act both as a sequestering agent and as an agent to control critical micelle concentration.

The antimicrobial sanitizing and disinfecting compositions of the present invention may be successfully employed in sanitizing and disinfecting food handling equipment and machinery such as that found in kitchens, dairies, breweries, food packing and canning facilities, beverage plants and the like. Moreover, the compositions of this invention can be used to prepare aqueous antimicrobial solutions for the direct sanitizing of foods such as fresh fruits and vegetables. In this embodiment, the acidic component of the formulations may contain compounds such as citric acid, ascorbic acid or erythorbic acid which retard the browning of fresh fruits and vegetables.

When enhanced with flavoring and sweetening agents, the concentrate compositions of this invention can be used to prepare aqueous disinfecting solutions for use as mouth washes and oral rinses. When combined with emolients, conditioning agents, perfumes and coloring agents, the compositions of this invention can be diluted either with water or with a suitable non-aqueous diluent for use as antimicrobial preparations for the hair, hands, and skin.

Dry, powdered concentrate compositions of this invention suitable for use in sanitizing and disinfecting food handling and processing equipment as well as in other applications where compatability with food for human and animal consumption is a prerequisite comprise from between about 1 part by weight to about 7.5 parts by weight anionic surfactant, with the balance comprising an acidic component selected from adipic acid, ascorbic acid, citric acid, hydroxyacetic acid, erythorbic acid, fumaric acid, glutaric acid, gluconic acid, lactic acid, malic acid, succinic acid, tannic acid, tartaric acid, and mixtures thereof.

Anhydrous liquid concentrate sanitizer formulations in accordance with this invention comprise from between about 0.05 weight percent to about 10 weight percent anionic surfactant component, from about 10 weight percent to about 35 weight percent acidic component, with the balance comprising an anhydrous solvent, preferably propylene glycol. The propylene glycol may be replaced by the acidic component, as in the case of glacial acetic acid, or propionic acid. Small amounts, ranging from about 0.1 weight percent to about 3 weight percent of a fatty acid of from eight to twelve carbon atoms may also be added to the mixture.

Dry, solid formulations particularly suited for dilution just prior to use as an oral rinse or mouthwash comprise from about 2 weight percent to about 3 weight percent of an anionic surfactant, from about 30 weight percent to about 35 weight percent citric acid, from about 7 weight percent to about 15 weight percent flavoring agent, and from about 20 weight percent to about 60 weight percent sweetener.

Depending upon the end use intended, in general, the concentrate formulations of the present invention are diluted with either water or a suitable non-aqueous diluent such as propylene glycol. Aqueous antimicrobial solutions are prepared, for example, by diluting from 0.25 parts by weight to about 10 parts by weight of the concentrate with sufficient water to make 100 parts of aqueous solution. For use as an oral rinse or mouthwash, between about 0.5 parts by weight to 2 parts by weight of the concentrate mixture are diluted with sufficient water to make 100 parts by weight. For use as an antimicrobial solution for sanitizing the surface of fresh fruits and vegetables, between about 1 and about 10 parts by weight of the concentrates of the present invention are diluted with sufficient water to make 100 parts by weight. For use as waterless antimicrobial preparations for the hands, hair, or skin, between about 1 weight percent and about 20 weight percent of the concentrates of this invention are diluted with sufficient non-aqueous diluent to make 100 parts by weight total. The concentrates can be diluted or mixed with suitable inert ingredients and molded into a bar for use as sanitizing bar soaps.

When the disinfecting and sanitizing compositions of this invention are diluted with water or other suitable non-aqueous solvents to form the solutions which are used in the various applications described above, it is preferred that the concentration of the anionic surfactant component in the diluted solution falls within the range of about 5 to about 500 parts per million.

Within this range of anionic surfactant concentration, the compositions of the present invention produce solutions in water or other suitable non-aqueous solvents having excellent antimicrobial activity against gram negative and gram positive bacteria as evidenced by the data presented below. In addition, the concentrated compositions of the present invention exhibit exceptional chemical stability and shelf life and are convenient to store and transport because of their small volume.

In tests of the stability of the compositions of the present invention, for example, no deterioration of the compositions or loss of antimicrobial activity upon dilution with water was observed even after allowing the concentrate mixtures to stand for periods of up to six months.

The following examples are provided to enable one skilled in the art to practice the invention.

SOLID SANITIZER OR DISINFECTANT FORMULATIONS

The following solid sanitizer/disinfectant formulations were prepared in accordance with the present invention. In each example, the indicated solid dry components were thoroughly mixed to form the solid formulation. For use as a sanitizing or disinfecting solution, the solid formulations were dissolved in water just prior to use.

| | Example 1 | |
|---|---|---|
| Dry Solid Formulation: | Sodium lauryl sulfate | (6.25 wt %) |
| | Anhydrous citric acid | (93.75 wt %) |
| Sanitizing/Disinfecting Solution: | 0.32–0.40 Parts by weight dry solid formulation | |
| | Water (to make 100 parts by weight) | |

| | Example 2 | |
|---|---|---|
| Dry Solid Formulation: | Sodium lauryl sulfate | (7.29 wt %) |
| | Anhydrous citric acid | (92.71 wt %) |
| Sanitizing/Disinfecting Solution: | 0.343 Parts by weight dry solid formulation | |
| | Water (to make 100 parts by weight) | |

| | Example 3 | |
|---|---|---|
| Dry Solid Formulation: | Sodium lauryl sulfate | (5.91 wt %) |
| | Anhydrous citric acid | (94.09 wt %) |
| Sanitizing/Disinfecting Solution: | 0.338 Parts by weight dry solid formulation | |
| | Water (to make 100 parts by weight) | |

| | Example 4 | |
|---|---|---|
| Dry Solid Formulation: | Sodium lauryl sulfate | (4.50 wt %) |
| | Anhydrous citric acid | (95.50 wt %) |
| Sanitizing/Disinfecting Solution: | 0.333 Parts by weight dry solid formulation | |
| | Water (to make 100 parts by weight) | |

| | Example 5 | |
|---|---|---|
| Dry Solid Formulation: | Sodium lauryl sulfate | (3.05 wt %) |
| | Anhydrous citric acid | (96.95 wt %) |
| Sanitizing/Disinfecting Solution: | 0.328 Parts by weight dry solid formulation | |
| | Water (to make 100 parts by weight) | |

| | Example 6 | |
|---|---|---|
| Dry Solid Formulation: | Sodium lauryl sulfate | (6.06 wt %) |

-continued

Example 6

| | | |
|---|---|---|
| | Anydrous citric acid | (90.90 wt %) |
| | Undecylenic acid | (3.03 wt %) |
| Sanitizing/Disinfecting Solution: | 0.32–0.40 Parts by weight dry solid formulation | |
| | Water (to make 100 parts by weight) | |

Example 7

| | | |
|---|---|---|
| Dry Solid Formulation: | Sodium lauryl sulfate | (6.15 wt %) |
| | Anhydrous citric acid | (92.31 wt %) |
| | Decanoic acid | (3.03 wt %) |
| Sanitizing/Disinfecting Solution: | 0.32–0.40 Parts by weight dry solid formulation | |
| | Water (to make 100 parts by weight) | |

Example 8

| | | |
|---|---|---|
| Dry Solid Formulation: | Sodium lauryl sulfate | (7.19 wt %) |
| | Anhydrous citric acid | (91.90 wt %) |
| | Decanoic acid or lauric acid | (0.99 wt %) |
| Sanitizing/Disinfecting Solution: | 0.40 Parts by weight dry solid formulation | |
| | Water (to make 100 parts by weight) | |

Example 9

| | | |
|---|---|---|
| Dry Solid Formulation: | Sodium lauryl sulfate | (0.48 wt %) |
| | Anhydrous citric acid | (65.70 wt %) |
| | Sodium citrate | (33.82 wt %) |
| Sanitizing/Disinfecting Solution: | 5.18 Parts by weight dry solid formulation | |
| | Water (to make 100 parts by weight) | |

Example 10

| | | |
|---|---|---|
| Dry Solid Formulation: | Sodium lauryl sulfate | (0.48 wt %) |
| | Anhydrous citric acid | (65.07 wt %) |
| | Dehydroacetic acid | (0.95 wt %) |
| | Sodium citrate | (33.49 wt %) |
| Sanitizing/Disinfecting Solution: | 5.23 Parts by weight dry solid formulation | |
| | Water (to make 100 parts by weight) | |

Example 11

| | | |
|---|---|---|
| Dry Solid Formulation: | Dioctyl sulfosuccinic acid | (3.4 wt %) |
| | Lactic acid | (96.60 wt %) |
| Sanitizing/Disinfecting Solution: | 0.88 Part by weight solid formulation | |
| | Water (to make 100 parts by weight) | |

Example 12

| | | |
|---|---|---|
| Dry Solid Formulation: | Octyl lactylate (Paniplus) | (3.4 wt %) |
| | Lactic acid | (96.6 wt %) |
| Sanitizing/Disinfecting Solution: | 0.88 Part by weight solid formulation | |
| | Water (to make 100 parts by weight) | |

Example 13

| | | |
|---|---|---|
| Dry Solid Formulation: | Octyl lactylate (Paniplus) | (1.7 wt %) |
| | Dioctyl sulfosuccinic acid | (1.7 wt %) |
| | Lactic acid | (96.6 wt %) |
| Sanitizing/Disinfecting Solution: | 0.88 Part by weight liquid formulation | |
| | Water (to make 100 parts by weight) | |

The sanitizing and disinfecting efficacy of the dilute aqueous solutions of the dry formulations of Example 2–5 above was evaluated using the procedure of Method No. 6 from the 13th Edition of the *Official Methods of Analysis of the A.O.A.C.*, 1111 North 19th Street, Alexandria, Va. 22209.

A concentrated suspension of Staphylococcus aureus or Escherichia coli was contacted with the reconstituted aqueous solutions of sanitizer/disinfectant from each example and aliquot samples were withdrawn after thirty and sixty seconds. These aliquot samples were plated on appropriate nutrient media, cultured and the resulting bacterial colonies counted to determine the number of surviving bacteria per milliliter. The results of these tests appear in Table 1.

TABLE 1

Microbiological Efficacy of Reconstitued Aqueous Solutions of Solid Sanitizer/Disinfectant Formulations of the Invention

| Example | Test | Bacterial Species | Initially | Number of Bacteria/mL After 30 sec. | After 60 sec. |
|---|---|---|---|---|---|
| 2 | 1 | Staphylococcus aureus | $77 \times 10^6$ | 1 | 0 |
| 2 | 2 | Staphylococcus aureus | $77 \times 10^6$ | 1 | 0 |
| 2 | 3 | Escherichia coli | $79 \times 10^6$ | 0 | 0 |
| 2 | 4 | Escherichia coli | $79 \times 10^6$ | 0 | 0 |
| 3 | 1 | Staphylococcus aureus | $77 \times 10^6$ | 5 | 0 |
| 3 | 2 | Staphylococcus aureus | $77 \times 10^6$ | 7 | 0 |
| 3 | 3 | Escherichia coli | $79 \times 10^6$ | 0 | 0 |
| 3 | 4 | Escherichia coli | $79 \times 10^6$ | 0 | 0 |
| 4 | 1 | Staphylococcus aureus | $77 \times 10^6$ | 19 | 1 |
| 4 | 2 | Staphylococcus aureus | $77 \times 10^6$ | 16 | 0 |
| 4 | 3 | Escherichia coli | $79 \times 10^6$ | 1 | 0 |
| 4 | 4 | Escherichia coli | $79 \times 10^6$ | 1 | 0 |
| 5 | 1 | Staphylococcus aureus | $77 \times 10^6$ | 105 | 3 |
| 5 | 2 | Staphylococcus aureus | $77 \times 10^6$ | 98 | 7 |
| 5 | 3 | Escherichia coli | $79 \times 10^6$ | 60 | 38 |
| 5 | 4 | Escherichia coli | $79 \times 10^6$ | 51 | 35 |

SOLID ORAL RINSE OR MOUTH WASH FORMULATION

Several solid oral rinse or mouth was concentrate formulations were prepared in accordance with the present invention by thoroughly mixing the components indicated in each of the following examples. For use as an oral rinse or mouth wash, the solid formulations were dissolved in water just prior to use.

Example 14

| | | |
|---|---|---|
| Dry Solid Formulation: | Sodium lauryl sulfate | (2.5 wt %) |
| | Anhydrous citric acid | (31.6 wt %) |
| | Saccharin | (1.5 wt %) |
| | FD&C Blue #1 powder | (0.2 wt %) |
| | Peppermint flavor powder | (5 wt %) |
| | Menthol | (4 wt %) |
| | Sorbitol | (55.2 wt %) |
| Oral rinse/mouth wash Solution: | 1 Part by weight dry solid formulation | |
| | Water (to make 100 parts by weight) | |

| Example 15 | | |
|---|---|---|
| Dry Solid Formulation: | Sodium lauryl sulfate | (2.5 wt %) |
| | Anhydrous citric acid | (31.6 wt %) |
| | Saccharin | (1.5 wt %) |
| | FD&C Red #40 powder | (0.4 wt %) |
| | Raspberry flavor powder | (8 wt %) |
| | Menthol | (2 wt %) |
| | Sorbitol | (54 wt %) |
| Oral rinse/mouth wash Solution: | 1 Part by weight dry solid formulation Water (to make 100 parts by weight) | |

| Example 16 | | |
|---|---|---|
| Dry Solid Formulation: | Sodium citric acid | (2.5 wt %) |
| | Anhydrous citric acid | (31.6 wt %) |
| | Saccharin | (1.5 wt %) |
| | FD&C Red #40 powder | (0.4 wt %) |
| | Raspberry flavor powder | (8 wt %) |
| | Menthol | (2 wt %) |
| | $ZnSO_4 \cdot 7H_2O$ | (30 wt %) |
| | Sorbitol | (24 wt %) |
| Oral rinse/mouth wash Solution: | 1 Part by weight dry solid formulation Water (to make 100 parts by weight) | |

| Example 17 | | |
|---|---|---|
| Dry Solid Formulation: | Sodium lauryl sulfate | (2.5 wt %) |
| | Anhydrous citric acid | (31.6 wt %) |
| | Saccharin | (1.5 wt %) |
| | FD&C Red #40 powder | (0.4 wt %) |
| | Raspberry flavor powder | (8 wt %) |
| | Menthol | (2 wt %) |
| | Sodium citrate | (10 wt %) |
| | $ZnSO_4 \cdot 7H_2O$ | (20 wt %) |
| | NaF | (5 wt %) |
| | Sorbitol | (19 wt %) |
| Oral rinse/mouth wash Solution: | 1 Part by weight dry solid formulation Water (to make 100 parts by weight) | |

The antimicrobial efficacy of the reconstituted aqueous solutions of the dry oral rinse or mouth wash formulations of Examples 15-17 above was evaluated using the procedure of Method No. 6 from the 13th Edition of the *Official Methods of Analysis of the A.O.A.C.*, 1111 North 19th Street, Alexandria, Va. 22209 described above. The results of these tests appear in Table 2.

TABLE 2

Microbiological Efficacy of Reconstituted Aqueous Solutions of Solid Oral Rinse/Mouth Wash Formulations of the Invention

| | | | | Number of Bacteria/mL | |
|---|---|---|---|---|---|
| Example | Test | Bacterial Species | Initially | After 30 sec. | After 60 sec. |
| 15 | 1 | Staphylococcus aureus | $77 \times 10^6$ | 0 | 0 |
| 15 | 2 | Staphylococcus aureus | $77 \times 10^6$ | 0 | 0 |
| 15 | 3 | Escherichia coli | $79 \times 10^6$ | 0 | 0 |
| 15 | 4 | Escherichia coli | $79 \times 10^6$ | 0 | 0 |
| 16 | 1 | Staphylococcus aureus | $77 \times 10^6$ | 0 | 0 |
| 16 | 2 | Staphylococcus aureus | $77 \times 10^6$ | 0 | 0 |
| 16 | 3 | Escherichia coli | $79 \times 10^6$ | 0 | 0 |
| 16 | 4 | Escherichia coli | $79 \times 10^6$ | 0 | 0 |
| 17 | 1 | Staphylococcus aureus | $77 \times 10^6$ | 1 | 0 |
| 17 | 2 | Staphylococcus aureus | $77 \times 10^6$ | 0 | 0 |
| 17 | 3 | Escherichia coli | $79 \times 10^6$ | 0 | 0 |
| 17 | 4 | Escherichia coli | $79 \times 10^6$ | 0 | 0 |

ANHYDROUS LIQUID SANITIZER OR DISINFECTANT FORMULATIONS

The following anhydrous liquid anitizer/disinfectant formulations in accordance with the present invention were prepared by thoroughly dissolving the indicated solid components in the indicated liquid component(s) to form an anhydrous sanitizer or disinfectant formulation. In Examples 18-22, the solid components were dissolved in propylene glycol as the solvent and had a solid acidic component. In Examples 20-26, the acidic component itself was liquid and served the dual function of solvent and acidic component. For use as a sanitizing or disinfecting solution, the liquid formulations were dissolved in water just prior to use at the concentrations indicated.

| Example 18 | | |
|---|---|---|
| Anhydrous Liquid Formulation: | Sodium lauryl sulfate | (3.0 wt %) |
| | Anhydrous citric acid | (29.0 wt %) |
| | Propylene glycol | (68.0 wt %) |
| Sanitizing/Disinfecting Solution: | 1.0 Part by weight liquid formulation Water (to make 100 parts by weight) | |

| Example 19 | | |
|---|---|---|
| Anhydrous Liquid Formulation: | Sodium lauryl sulfate | (4.0 wt %) |
| | Anhydrous citric acid | (29.0 wt %) |
| | Propylene glycol | (66.0 wt %) |
| | Octanoic/decanoic acid mixture (Emery 6358) | (1.0 wt %) |
| Sanitizing/Disinfecting Solution: | 1.0 Part by weight liquid formulation Water (to make 100 parts by weight) | |

| Example 20 | | |
|---|---|---|
| Anhydrous Liquid Formulation: | Sodium lauryl sulfate | (4.0 wt %) |
| | Anhydrous citric acid | (29.0 wt %) |
| | Propylene glycol | (66.0 wt %) |
| | Decanoic acid | (1.0 wt %) |
| Sanitizing/Disinfecting Solution: | 1.0 Part by weight liquid formulation Water (to make 100 parts by weight) | |

| Example 21 | | |
|---|---|---|
| Anhydrous Liquid Formulation: | Sodium lauryl sulfate | (4.0 wt %) |
| | Anhydrous citric acid | (29.0 wt %) |
| | Propylene glycol | (66.0 wt %) |
| | Undecylenic acid | (1.0 wt %) |
| Sanitizing/Disinfecting Solution: | 1.0 Part by weight liquid formulation Water (to make 100 parts by weight) | |

| Example 22 | | |
|---|---|---|
| Anhydrous Liquid Formulation: | Sulfosuccinic acid, dioctyl ester | (4.0 wt %) |
| | Anhydrous citric acid | (29.0 wt %) |
| | Propylene glycol | (67.0 wt %) |
| Sanitizing/Disinfecting Solution: | 1.0 Part by weight liquid formulation Water (to make 100 parts by weight) | |

| Example 23 | | |
|---|---|---|
| Anhydrous Liquid Formulation: | Dioctyl sulfosuccinic acid | (3.0 wt %) |
| | Glacial acetic acid | (97 wt %) |
| Sanitizing/Disinfecting Solution: | 1.0 Part by weight liquid formulation Water (to make 100 parts by weight) | |

Example 24

| | | |
|---|---|---|
| Anhydrous Liquid Formulat | Octyl lactylate (Paniplus) | (1.5 wt %) |
| | Dioctyl sulfosuccinic acid | (1.5 wt %) |
| | Glacial acetic acid | (97 wt %) |
| Sanitizing/Disinfecting Solution: | 1.0 Part by weight liquid formulation Water (to make 100 parts by weight) | |

Example 25

| | | |
|---|---|---|
| Anhydrous Liquid Formulate | Octyl lactylate (Paniplus) | (3.0 wt %) |
| | Glacial acetic acid | (97 wt %) |
| Sanitizing/Disinfecting Solution: | 1.0 Part by weight liquid formulation Water (to make 100 parts by weight) | |

Example 26

| | | |
|---|---|---|
| Anhydrous Liquid Formulate | Octyl lactylate (Paniplus) | (3.0 wt %) |
| | Dehydroacetic acid | (5.0 wt %) |
| | Glacial acetic acid | (92.0 wt %) |
| Sanitizing/Disinfecting Solution: | 1.0 Part by weight liquid formulation Water (to make 100 parts by weight) | |

SOLID SALAD FRESHENER/SANITIZER FORMULATIONS

Example 27

| | | |
|---|---|---|
| Dry Solid Formulation: | Sodium lauryl sulfate | (1.79 wt %) |
| | Anhydrous citric acid | (26.78 wt %) |
| | Ascorbic acid | (71.43 wt %) |
| Sanitizing/Disinfecting Solution: | 1.4 Parts by weight dry solid formulation Water (to make 100 parts by weight) | |

Example 28

| | | |
|---|---|---|
| Dry Solid Formulation: | Sodium lauryl sulfate | (1.79 wt %) |
| | Anhydrous citric acid | (26.78 wt %) |
| | Erythorbic acid | (71.43 wt %) |
| Sanitizing/Disinfecting Solution: | 1.4 Parts by weight dry solid formulation Water (to make 100 parts by weight) | |

Example 29

| | | |
|---|---|---|
| Dry Solid Formulation: | Sodium lauryl sulfate | (0.46 wt %) |
| | Anhydrous citric acid | (6.95 wt %) |
| | Ascorbic acid | (92.59 wt %) |
| Sanitizing/Disinfecting Solution: | 5.4 Parts by weight dry solid formulation Water (to make 100 parts by weight) | |

Example 30

| | | |
|---|---|---|
| Dry Solid Formulation: | Sodium lauryl sulfate | (0.46 wt %) |
| | Anhydrous citric acid | (6.95 wt %) |
| | Erythorbic acid | (92.59 wt %) |
| Sanitizing/Disinfecting Solution: | 5.4 Parts by weight dry solid formulation Water (to make 100 parts by weight) | |

Example 31

| | | |
|---|---|---|
| Dry Solid Formulation: | Sodium lauryl sulfate | (0.95 wt %) |
| | Ascorbic acid | (38.09 wt %) |
| | Sodium sulfate | (60.95 wt %) |
| Sanitizing/Disinfecting Solution: | 2.63 Parts by weight dry solid formulation Water (to make 100 parts by weight) | |

Example 32

| | | |
|---|---|---|
| Dry Solid Formulation: | Sodium lauryl sulfate | (0.95 wt %) |
| | Erythorbic acid | (38.09 wt %) |
| | Sodium sulfate | (60.95 wt %) |
| Sanitizing/Disinfecting Solution: | 2.63 Parts by weight dry solid formulation Water (to make 100 parts by weight) | |

Example 33

| | | |
|---|---|---|
| Dry Solid Formulation: | Sodium lauryl sulfate | (0.85 wt %) |
| | Citric acid | (10.82 wt %) |
| | Ascorbic acid | (33.97 wt %) |
| | Sodium sulfate | (54.35 wt %) |
| Sanitizing/Disinfecting Solution: | 2.94 Parts by weight dry solid formulation Water (to make 100 parts by weight) | |

Example 34

| | | |
|---|---|---|
| Dry Solid Formulation: | Sodium lauryl sulfate | (0.85 wt %) |
| | Citric acid | (10.82 wt %) |
| | Erythorbic acid | (33.97 wt %) |
| | Sodium sulfate | (54.35 wt %) |
| Sanitizing/Disinfecting Solution: | 2.94 Parts by weight dry solid formulation Water (to make 100 parts by weight) | |

Example 35

| | | |
|---|---|---|
| Dry Solid Formulation: | Sodium lauryl sulfate | (1.06 wt %) |
| | Citric acid | (13.54 wt %) |
| | Ascorbic acid | (42.60 wt %) |
| | Lauric acid | (0.17 wt %) |
| | Sodium acid pyrophosphate | (42.60 wt %) |
| Sanitizing/Disinfecting Solution: | 2.35 Parts by weight dry solid formulation Water (to make 100 parts by weight) | |

Example 36

| | | |
|---|---|---|
| Dry Solid Formulation: | Sodium lauryl sulfate | (1.06 wt %) |
| | Citric acid | (13.54 wt %) |
| | Erythorbic acid | (42.60 wt %) |
| | Lauric acid | (0.17 wt %) |
| | Sodium acid pyrophosphate | (42.60 wt %) |
| Sanitizing/Disinfecting Solution: | 2.35 Parts by weight dry solid formulation Water (to make 100 parts by weight) | |

Example 37

| | | |
|---|---|---|
| Dry Solid Formulation: | Sodium lauryl sulfate | (1.85 wt %) |
| | Citric acid | (23.60 wt %) |
| | Ascorbic acid | (74.23 wt %) |
| | Lauric acid | (0.29 wt %) |
| Sanitizing/Disinfecting Solution: | 1.35 Parts by weight dry solid formulation Water (to make 100 parts by weight) | |

| | Example 38 | |
|---|---|---|
| Dry Solid Formulation: | Sodium lauryl sulfate | (1.85 wt %) |
| | Citric acid | (23.60 wt %) |
| | Erythorbic acid | (74.23 wt %) |
| | Lauric acid | (0.29 wt %) |
| Sanitizing/Disinfecting Solution: | 1.35 Parts by weight dry solid formulation | |
| | Water (to make 100 parts by weight) | |

| | Example 39 | |
|---|---|---|
| Dry Solid Formulation: | Sodium lauryl sulfate | (0.82 wt %) |
| | Citric acid | (33.01 wt %) |
| | Ascorbic acid | (33.01 wt %) |
| | Lauric acid | (0.13 wt %) |
| | Sodium acid pyrophosphate | (33.01 wt %) |
| Sanitizing/Disinfecting Solution: | 3.04 Parts by weight dry solid formulation | |
| | Water (to make 100 parts by weight) | |

| | Example 40 | |
|---|---|---|
| Dry Solid Formulation: | Sodium lauryl sulfate | (0.82 wt %) |
| | Citric acid | (33.01 wt %) |
| | Erythorbic acid | (33.01 wt %) |
| | Lauric acid | (0.13 wt %) |
| | Sodium acid pyrophosphate | (33.01 wt %) |
| Sanitizing/Disinfecting Solution: | 3.04 Parts by weight dry solid formulation | |
| | Water (to make 100 parts by weight) | |

| | Example 41 | |
|---|---|---|
| Dry Solid Formulation: | Sodium lauryl sulfate | (1.23 wt %) |
| | Citric acid | (49.28 wt %) |
| | Ascorbic acid | (49.28 wt %) |
| | Lauric acid | (0.20 wt %) |
| Sanitizing/Disinfecting Solution: | 2.03 Parts by weight dry solid formulation | |
| | Water (to make 100 parts by weight) | |

| | Example 42 | |
|---|---|---|
| Dry Solid Formulation: | Sodium lauryl sulfate | (1.23 wt %) |
| | Citric acid | (49.28 wt %) |
| | Erythorbic acid | (49.28 wt %) |
| | Lauric acid | (0.20 wt %) |
| Sanitizing/Disinfecting Solution: | 2.03 Parts by weight dry solid formulation | |
| | Water (to make 100 parts by weight) | |

| | Example 43 | |
|---|---|---|
| Dry Solid Formulation: | Sodium lauryl sulfate | (0.43 wt %) |
| | Citric acid | (13.68 wt %) |
| | Ascorbic acid | (42.91 wt %) |
| | Lauric acid | (0.07 wt %) |
| | Sodium acid pyrophosphate | (42.91 wt %) |
| Sanitizing/Disinfecting Solution: | 2.33 Parts by weight dry solid formulation | |
| | Water (to make 100 parts by weight) | |

| | Example 44 | |
|---|---|---|
| Dry Solid Formulation: | Sodium lauryl sulfate | (0.43 wt %) |
| | Citric acid | (13.68 wt %) |
| | Erythorbic acid | (42.91 wt %) |
| | Lauric acid | (0.07 wt %) |
| | Sodium acid pyrophosphate | (42.91 wt %) |
| Sanitizing/Disinfecting Solution: | 2.33 Parts by weight dry solid formulation | |
| | Water (to make 100 parts by weight) | |

| | Example 45 | |
|---|---|---|
| Dry Solid Formulation: | Sodium lauryl sulfate | (0.75 wt %) |
| | Citric acid | (23.91 wt %) |
| | Ascorbic acid | (75.21 wt %) |
| | Lauric acid | (0.12 wt %) |
| Sanitizing/Disinfecting Solution: | 1.33 Parts by weight dry solid formulation | |
| | Water (to make 100 parts by weight) | |

| | Example 46 | |
|---|---|---|
| Dry Solid Formulation: | Sodium lauryl sulfate | (0.75 wt %) |
| | Citric acid | (23.91 wt %) |
| | Erythorbic acid | (75.21 wt %) |
| | Lauric acid | (0.12 wt %) |
| Sanitizing/Disinfecting Solution: | 1.33 Parts by weight dry solid formulation | |
| | Water (to make 100 parts by weight) | |

| | Example 47 | |
|---|---|---|
| Dry Solid Formulation: | Sodium lauryl sulfate | (0.33 wt %) |
| | Citric acid | (33.20 wt %) |
| | Ascorbic acid | (33.20 wt %) |
| | Lauric acid | (0.05 wt %) |
| | Sodium acid pyrophosphate | (33.20 wt %) |
| Sanitizing/Disinfecting Solution: | 3.03 Parts by weight dry solid formulation | |
| | Water (to make 100 parts by weight) | |

| | Example 48 | |
|---|---|---|
| Dry Solid Formulation: | Sodium lauryl sulfate | (0.33 wt %) |
| | Citric acid | (33.20 wt %) |
| | Erythorbic acid | (33.20 wt %) |
| | Lauric acid | (0.05 wt %) |
| | Sodium acid pyrophosphate | (33.20 wt %) |
| Sanitizing/Disinfecting Solution: | 3.03 Parts by weight dry solid formulation | |
| | Water (to make 100 parts by weight) | |

| | Example 49 | |
|---|---|---|
| Dry Solid Formulation: | Sodium lauryl sulfate | (0.49 wt %) |
| | Citric acid | (49.71 wt %) |
| | Ascorbic acid | (49.71 wt %) |
| | Lauric acid | (0.08 wt %) |
| Sanitizing/Disinfecting Solution: | 2.03 Parts by weight dry solid formulation | |
| | Water (to make 100 parts by weight) | |

| Example 50 | | |
|---|---|---|
| Dry Solid Formulation: | Sodium lauryl sulfate | (0.49 wt %) |
| | Citric acid | (49.71 wt %) |
| | Erythorbic acid | (49.71 wt %) |
| | Lauric acid | (0.08 wt %) |
| Sanitizing/Disinfecting Solution: | 2.03 Parts by weight dry solid formulation | |
| | Water (to make 100 parts by weight) | |

| Example 51 | | |
|---|---|---|
| Dry Solid Formulation: | Sodium lauryl sulfate | (0.59 wt %) |
| | Erythorbic acid | (23.66 wt %) |
| | Citric acid | (23.66 wt %) |
| | Sodium acid pyrophosphate | (49.73 wt %) |
| | Benzoic acid | (2.36 wt %) |
| Sanitizing/Disinfecting Solution | 1.7 Parts by weight dry solid formulation | |
| | Water (to make 100 parts by weight) | |

| Example 52 | | |
|---|---|---|
| Dry Solid Formulation: | Sodium lauryl sulfate | (0.32 wt %) |
| | Erythorbic acid | (32.15 wt %) |
| | Citric acid | (32.15 wt %) |
| | Sodium acid pyrophosphate | (32.15 wt %) |
| | Benzoic acid | (3.23 wt %) |
| Sanitizing/Disinfecting Solution | 3.12 Parts by weight dry solid formulation | |
| | Water (to make 100 parts by weight) | |

| Example 53 | | |
|---|---|---|
| Dry Solid Formulation | Sodium lauryl sulfate | (0.62 wt %) |
| | Erythorbic or ascorbic acid | (24.84 wt %) |
| | Citric acid | (24.84 wt %) |
| | Sodium acid pyrophosphate | (49.69 wt %) |
| Sanitizing/Disinfecting Solution | 4.03 Parts by weight dry solid formulation | |
| | Water (to make 100 parts by weight) | |

The antimicrobial efficacy of the reconstituted aqueous solutions of the dry salad freshener or sanitizer formulations of Examples 31-34 above was evaluated using the procedure of Method No. 6 from the 13th Edition of the *Official Methods of Analysis of the A.O.A.C.*, 1111 North 19th Street, Alexandria, Va. 22209 described above. The results of these tests appear in Table 3.

TABLE 3

Microbiological Efficacy of Reconstituted Aqueous Solutions of Solid Salad Freshener/Sanitizer Formulations of the Invention

| | | | | Number of Bacteria/mL | |
|---|---|---|---|---|---|
| Example | Test | Bacterial Species | Initially | After 30 sec. | After 60 sec. |
| 31 | 1 | Staphyloccocus aureus | $77 \times 10^6$ | 2 | 0 |
| 31 | 2 | Staphylococcus aureus | $77 \times 10^6$ | 1 | 0 |
| 31 | 3 | Escherichia coli | $79 \times 10^6$ | 0 | 0 |
| 31 | 4 | Escherichia coli | $79 \times 10^6$ | 0 | 0 |
| 32 | 1 | Staphylococcus aureus | $77 \times 10^6$ | 6 | 0 |
| 32 | 2 | Staphylococcus aureus | $77 \times 10^6$ | 0 | 0 |
| 32 | 3 | Escherichia coli | $79 \times 10^6$ | 0 | 0 |
| 32 | 4 | Escherichia coli | $79 \times 10^6$ | 0 | 0 |
| 33 | 1 | Staphylococcus aureus | $77 \times 10^6$ | 0 | 0 |
| 33 | 2 | Staphylococcus aureus | $77 \times 10^6$ | 0 | 0 |
| 33 | 3 | Escherichia coli | $79 \times 10^6$ | 0 | 0 |
| 33 | 4 | Escherichia coli | $79 \times 10^6$ | 0 | 0 |
| 34 | 1 | Staphylococcus aureus | $77 \times 10^6$ | 2 | 0 |
| 34 | 2 | Staphylococcus aureus | $77 \times 10^6$ | 0 | 0 |
| 34 | 3 | Escherichia coli | $79 \times 10^6$ | 0 | 0 |
| 34 | 4 | Escherichia coli | $79 \times 10^6$ | 0 | 0 |

The examples presented above are merely illustrative and should not be read as limiting the scope of the invention as it is defined in the appended claims.

I claim:

1. An anhydrous disinfecting and sanitizing dry powder concentrate composition having improved shelf life and stability, capable of dilution with water to form an antimicrobial solution, the concentrate composition consisting essentially of:
   a) an anionic surfactant present in an amount of from about 0.025 weight percent to about 7.5 weight percent, based on the total weight of the concentrate composition;
   b) an acidic component, present in an amount effective to produce a pH of below pH 5.0 upon dilution with water to make an aqueous alcohol free mouthwash solution of the concentrate and such that said anionic surfactant is present in solution at about 0.0025% to about 0.075%.

2. An anhydrous disinfecting and sanitizing concentrate as defined by claim 1 wherein said anionic surfactant is selected from the group consisting of the ammonium, sodium, potassium, calcium and magnesium salts of
   (a) $C_6$-$C_{18}$ alkyl- and alkenylsulfates;
   (b) $C_6$-$C_{18}$ alkyl- and alkenyl ether sulfates;
   (c) $C_8$-$C_{16}$ alkyl diphenyl ether disulfonates;
   (d) $C_4$-$C_{18}$ fatty acid isethionates;
   (e) $C_6$-$C_{18}$ alkyl- and alkenylsulfonates;
   (f) dialkyl- and dialkenyl sulfosuccinates in which the alkyl or alkenyl groups independently contain from six to eighteen carbon atoms;
   (g) alkylbenzenesulfonates in which the alkyl group contain from six to eighteen carbon atoms;
   (h) naphthalenesulfonates;
   (i) alkylnaphthalenesulfonates in which the alkyl group contains from one to six carbon atoms;
   (j) the mono-(n-alkyl) and mono-(n-alkenyl) acyl esters of $C_2$-$C_4$ hydroxylated monocarboxylic acids, in which the alkyl or alkenyl group contains from six to eighteen carbon atoms;
   (k) the mono-(n-alkyl) and mono-(n-alkenyl) acyl esters of $C_2$-$C_4$ hydroxylated dicarboxylic acids, in which the alkyl or alkenyl group contains from six to eighteen carbon atoms;
   (l) the mono-(n-alkyl) and mono-(n-alkenyl) alkyl esters of $C_2$-$C_4$ dicarboxylic acids, in which the alkyl or alkenyl group contains from six to eighteen carbon atoms, and
   (m) $C_4$-$C_{18}$ fatty alcohol sulfoacetates.

3. An anhydrous disinfecting and sanitizing concentrate as defined by claim 2 wherein said anionic surfactant is selected from sodium 1,4-dihexyl sulfosuccinate, sodium dioctylsulfosuccinate, sodium laurylsulfate, and octyl lactylate.

4. An anhydrous disinfecting and sanitizing concentrate as defined by claim 1 wherein said acidic component is selected from the group consisting of acetic acid, adipic acid, ascorbic acid, citric acid, dehydroacetic acid, erythorbic acid, fumaric acid, glutaric acid, gluconic acid, hyaluronic acid, hydroxyacetic acid, lactic acid, malic acid, succinic acid, sulfamic acid, tannic acid, tartaric acid, and mixtures thereof.

5. An anhydrous disinfecting and sanitizing concentrate as defined by claim 1 further comprising a salt selected from the group consisting of sodium acid pyrophosphate and the chlorides, sulfates, citrates, nitrates, acetates, and lactates of potassium, sodium, ammonium, and zinc.

6. A dry, solid disinfecting and sanitizing powder concentrate consisting essentially of between about 0.025 and about 7.5 weight percent anionic surfactant, the balance comprising an acidic component selected from the group consisting of acetic acid, adipic acid, ascorbic acid, citric acid, dehydroacetic acid, erythorbic acid, fumaric acid, glutaric acid, gluconic acid, hyaluronic acid, hydroxyacetic acid, lactic acid, malic acid, succinic acid, sulfamic acid, tannic acid, tartaric acid, and mixtures thereof such that upon dilution with an alcohol free mouthwash solution pH is below 5.0 and the anionic surfactant is present in solution at about 0.0025% to about 0.075%.

7. A dry, solid disinfecting and sanitizing concentrate as defined by claim 6 wherein said anionic surfactant is selected from the group consisting of the ammonium, sodium, potassium, calcium and magnesium salts of
  (a) $C_6$–$C_{18}$ alkyl- and alkenylsulfates;
  (b) $C_6$–$C_{18}$ alkyl- and alkenyl ether sulfates;
  (c) $C_8$–$C_{16}$ alkyl diphenyl ether disulfonates;
  (d) $C_4$–$C_{18}$ fatty acid isethionates;
  (e) $C_6$–$C_{18}$ alkyl- and alkenylsulfonates;
  (f) dialkyl- and dialkenyl sulfosuccinates in which the alkyl or alkenyl groups independently contain from six to eighteen carbon atoms;
  (g) alkylbenzenesulfonates in which the alkyl group contain from six to eighteen carbon atoms;
  (h) naphthalenesulfonates;
  (i) alkylnaphthalenesulfonates in which the alkyl group contains from one to six carbon atoms;
  (j) the mono-(n-alkyl) and mono-(n-alkenyl) acyl esters of $C_2$–$C_4$ hydroxylated monocarboxylic acids, in which the alkyl or alkenyl group contains from six to eighteen carbon atoms;
  (k) the mono-(n-alkyl) and mono-(n-alkenyl) acyl esters of $C_2$–$C_4$ hydroxylated dicarboxylic acids, in which the alkyl or alkenyl group contains from six to eighteen carbon atoms;
  (l) the mono-(n-alkyl) and mono-(n-alkenyl) alkyl esters of $C_2$–$C_4$ dicarboxylic acids, in which the alkyl or alkenyl group contains from six to eighteen carbon atoms, and
  (m) $C_4$–$C_{18}$ fatty alcohol sulfoacetates.

8. A dry, solid disinfecting and sanitizing concentrate as defined by claim 7 wherein said anionic surfactant is selected from sodium 1,4-dihexyl sulfosuccinate, sodium dioctylsulfosuccinate, sodium laurylsulfate, and octyl lactylate.

9. A dry, solid disinfecting and sanitizing powder concentrate suitable for dilution with water to form an oral rinse or mouthwash solution consisting essentially of
  a) from about 0.025 weight percent to about 7.5 weight percent anionic surfactant;
  b) from about 6.95 weight percent to about 35 weight percent citric acid;
  c) from about 7 weight percent to about 15 weight percent flavoring agent; and
  d) from about 20 weight percent to about 60 weight percent sweetening agent such that upon dilution said anionic surfactant is present in an alcohol free mouthwash solution at about 0.0025% to about 0.075%.

10. A dry, solid disinfecting and sanitizing concentrate as defined by claim 9, wherein said anionic surfactant is selected from the group consisting of sodium 1,4-dihexyl sulfosuccinate, sodium dioctylsulfosuccinate, sodium laurylsulfate, and octyl lactylate.

* * * * *